(12) United States Patent
Kalagias

(10) Patent No.: US 8,143,458 B2
(45) Date of Patent: Mar. 27, 2012

(54) PROCESSES FOR ISOLATING OR PURIFYING PROPYLENE GLYCOL, ETHYLENE GLYCOL AND PRODUCTS PRODUCED THEREFROM

(75) Inventor: Peter Kalagias, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 1042 days.

(21) Appl. No.: 11/926,691

(22) Filed: Oct. 29, 2007

(65) Prior Publication Data
US 2008/0275277 A1    Nov. 6, 2008

Related U.S. Application Data

(60) Provisional application No. 60/854,987, filed on Oct. 27, 2006.

(51) Int. Cl.
     *C07C 29/80*      (2006.01)
(52) U.S. Cl. .................. 568/854; 568/861; 568/868
(58) Field of Classification Search .................. 568/868, 568/861, 854; 203/57, 68; 202/152
See application file for complete search history.

(56) References Cited

U.S. PATENT DOCUMENTS

| | | | |
|---|---|---|---|
| 4,028,195 A | 6/1977 | Becker et al. | |
| 4,401,823 A | 8/1983 | Arena | |
| 4,476,331 A | 10/1984 | Dubeck et al. | |
| 4,642,394 A | 2/1987 | Che | |
| 4,935,102 A | 6/1990 | Berg | |
| 4,966,658 A | 10/1990 | Berg | |
| 5,026,927 A | 6/1991 | Andrews et al. | |
| 5,214,219 A * | 5/1993 | Casale et al. ............... | 568/861 |
| 5,276,181 A | 1/1994 | Casale et al. | |
| 5,354,914 A | 10/1994 | Gubitosa et al. | |
| 5,423,955 A | 6/1995 | Berg | |
| 5,425,853 A * | 6/1995 | Berg ........................... | 203/57 |
| 5,616,817 A | 4/1997 | Schuster et al. | |
| 6,291,725 B1 | 9/2001 | Chopade et al. | |
| 6,479,713 B1 | 11/2002 | Werpy et al. | |
| 7,126,034 B2 | 10/2006 | Meng et al. | |
| 2005/0069997 A1* | 3/2005 | Adkesson et al. ............ | 435/158 |
| 2005/0244312 A1 | 11/2005 | Suppes et al. | |

FOREIGN PATENT DOCUMENTS

| | | |
|---|---|---|
| DE | 541362 C | 12/1931 |
| EP | 0415202 A2 | 3/1991 |
| EP | 0415202 A3 | 2/1992 |
| EP | 0523014 A2 | 1/1993 |
| EP | 0523014 A3 | 1/1993 |
| EP | 0415202 81 | 6/1994 |
| GB | 992165 A | 5/1965 |
| WO | 2005051874 A1 | 6/2005 |

OTHER PUBLICATIONS

Federal Register, vol. 70, No. 7, Jan. 2005, Rules and Regulations, pp. 1792-1812.
Miyazawa, Kusunoki, Kunimori, Tomishige, Glycerol conversion in the aqueous solution under hydrogen over Ru/C + an ion-exchange resin and its reaction mechanism, Journal of Catalysis, Mar. 2006, pp. 213-221, www.sciencedirect.com, USA.
Montassier, Dumas, Granger, Barbier, Deactivation of supported copper based catalysts during polyol conversion in aqueous phase, Applied Catalysis A:General 121, Sep. 1995, pp. 231-244, Elsevier.
Montassier, Menezo, Moukolo, Naja, Hoang, Barbier, Boitiaux, Polyol conversions into furanic derivatives on bimetallic catalysts: Cu-Ru, Cu-Pt and Ru-Cu, Journal of Molecular Catalysis, 70 (1991) pp. 65-84, Elsevier Sequoia, Lausanne.
Guisnet , ed, Polyol Conversion by Liquid Phase Heterogeneous Catalysis Over Metals, 1988, Montassier, Giraud, Barbier, pp. 165-170, Stud. Surf. Sci. Catalysis 41, Elsevier Science Publishers, The Netherlands.
Perosa and Tundo, Selective Hydrogenlysis of Glycerol with Raney Nickel, Ind. Eng. Chem. Res., 2005, 44, pp. 8535-8537, American Chemical Society, USA.
Kusunoki, Miyazawa, Kunimori, Tomishige, Highly active metal-acid bifunctional catalyst sytem for hydrogenolysis of glycerol under mild reaction conditions, Catalysis Communications 6, 2005, pp. 645-649, www.sciencedirect.com, Elsevier Ltd., USA.
Montassier, Giraud, Barbier Boitiaux, Polyol conversion by liquid phase heterogeneous catalysis over metals, Bulletin de la Societe Chimique de France, 2 (1989) pp. 148-155.
Extractive distillation, Wikipedia, Dec. 2007, USA.
Standard Test Methods for Determining the Biobased Content of Natural Range Materials Using Radiocarbon and Isotope Ratio Mass Spectrometry Analysis, ASTM International Designation: D 6866-05, 2005, pp. 1-14, USA.
Crabtree, Lawrence, Tuck and Tyers, Optimize glycol production from biomass, A novel glycol production method provides a way to use glycerol—the unwanted byproduct from biodiesel processing, Clean Fuels Special Report, Hydrocarbon Processing Feb. 2006, pp. 87-92, USA.
Written Opinion of the International Searching Authority and International Search Report for International Application No. PCT/US2007/022815. European Patent Office (acting as International Searching Authority), 8 pages, Apr. 2008.

* cited by examiner

*Primary Examiner* — Sikarl Witherspoon
(74) *Attorney, Agent, or Firm* — William B. Muller

(57) ABSTRACT

Processes for separating butanediols from glycols are disclosed, as well as products and compositions resulting therefrom.

5 Claims, 17 Drawing Sheets

| PG RECTIFICATION | | | | | |
|---|---|---|---|---|---|
| Stream ID | | 1 | 2,3BDO | 4 | Water |
| Temperature | F | 100.0 | 182.0 | 303.2 | 300.0 |
| Pressure | psi | 40.00 | 3.87 | 4.06 | 20.00 |
| Vapor Frac | | 0.000 | 0.000 | 0.000 | 1.000 |
| Mole Flow | lbmol/hr | 449.920 | 5.361 | 444.614 | 0.056 |
| Mass Flow | lb/hr | 34000.000 | 301.004 | 33699.996 | 1.000 |
| Volume Flow | cuft/hr | 534.983 | 4.893 | 604.072 | 22.468 |
| Enthalpy | MMBtu/hr | -93.784 | -0.948 | -88.756 | -0.006 |
| Mass Flow | lb/hr | | | | |
| 23BD | | 170.000 | 37.705 | 132.295 | |
| PG | | 33082.000 | 228.065 | 32853.935 | |
| 12BD | | 34.000 | 0.234 | 33.766 | |
| EG | | 680.000 | trace | 680.000 | |
| Water | | 34.000 | 35.000 | trace | 1.000 |
| P-XLY-01 | | | | | |
| Metha-01 | | | | | |
| Ethan-01 | | | | | |
| 1-PRO-01 | | | | | |
| Mass Frac | | | | | |
| 23BD | | 0.005 | 0.125 | 0.004 | |
| PG | | 0.973 | 0.758 | 0.975 | |
| 12BD | | 0.001 | 779PPM | 0.001 | |
| EG | | 0.020 | trace | 0.020 | |
| Water | | 0.001 | 0.116 | trace | 1.000 |
| P-XLY-01 | | | | | |
| Metha-01 | | | | | |
| Ethan-01 | | | | | |
| 1-PRO-01 | | | | | |
| Mole Flow | lbmol/hr | | | | |
| 23BD | | 1.886 | 0.418 | 1.468 | |
| PG | | 434.744 | 2.997 | 431.747 | |
| 12BD | | 0.447 | 0.003 | 0.444 | |
| EG | | 10.956 | trace | 10.956 | |
| Water | | 1.887 | 1.943 | trace | 0.056 |
| P-XLY-01 | | | | | |
| Metha-01 | | | | | |
| Ethan-01 | | | | | |
| 1-PRO-01 | | | | | |

FIGURE 1B

| PG RECTIFICATION | | | | | |
|---|---|---|---|---|---|
| Stream ID | | 1 | 2,3BDO | 4 | Water |
| Temperature | F | 100.0 | 153.0 | 303.3 | 300.0 |
| Pressure | psi | 40.00 | 3.87 | 4.06 | 20.00 |
| Vapor Frac | | 0.000 | 0.000 | 0.000 | 1.000 |
| Mole Flow | lbmol/hr | 449.920 | 49.453 | 444.874 | 44.407 |
| Mass Flow | lb/hr | 34000.000 | 1100.000 | 33700.000 | 800.000 |
| Volume Flow | cuft/hr | 534.983 | 18.198 | 604.072 | 17974.347 |
| Enthalpy | MMBtu/hr | -93.784 | -6.323 | -88.773 | -4.538 |
| Mass Flow | lb/hr | | | | |
| 23BD | | 170.000 | 164.456 | 5.544 | |
| PG | | 33082.000 | 101.440 | 32980.560 | |
| 12BD | | 34.000 | 0.010 | 33.896 | |
| EG | | 680.000 | trace | 680.000 | |
| Water | | 34.000 | 834.000 | trace | 800.000 |
| P-XLY-01 | | | | | |
| Metha-01 | | | | | |
| Ethan-01 | | | | | |
| 1-PRO-01 | | | | | |
| Mass Frac | | | | | |
| 23BD | | 0.005 | 0.150 | 165PPM | |
| PG | | 0.973 | 0.092 | 0.098 | |
| 12BD | | 0.001 | 95PPM | 0.001 | |
| EG | | 0.020 | trace | 0.020 | |
| Water | | 0.001 | 0.758 | trace | 1.000 |
| P-XLY-01 | | | | | |
| Metha-01 | | | | | |
| Ethan-01 | | | | | |
| 1-PRO-01 | | | | | |
| Mole Flow | lbmol/hr | | | | |
| 23BD | | 1.886 | 1.825 | 0.062 | |
| PG | | 434.744 | 1.333 | 433.411 | |
| 12BD | | 0.447 | 0.001 | 0.445 | |
| EG | | 10.956 | trace | 10.956 | |
| Water | | 1.887 | 46.294 | trace | 44.407 |
| P-XLY-01 | | | | | |
| Metha-01 | | | | | |
| Ethan-01 | | | | | |
| 1-PRO-01 | | | | | |

FIGURE 2B

| PG RECTIFICATION |||||
|---|---|---|---|---|---|
| Stream ID | | 1 | 2,3BDO | 4 | Methanol |
| Temperature | F | 100.0 | 99.2 | 303.2 | 300.0 |
| Pressure | psi | 40.00 | 3.87 | 4.06 | 20.00 |
| Vapor Frac | | 0.000 | 0.000 | 0.000 | 1.000 |
| Mole Flow | lbmol/hr | 449.920 | 30.070 | 444.817 | 24.967 |
| Mass Flow | lb/hr | 34000.000 | 1100.000 | 33700.000 | 800.000 |
| Volume Flow | cuft/hr | 534.983 | 20.948 | 604.031 | 10073.881 |
| Enthalpy | MMBtu/hr | -93.784 | -3.491 | -88.769 | -2.093 |
| Mass Flow | lb/hr | | | | |
| 23BD | | 170.000 | 136.814 | 33.186 | |
| PG | | 33082.000 | 129.053 | 32952.947 | |
| 12BD | | 34.000 | 0.133 | 33.867 | |
| EG | | 680.000 | trace | 680.000 | |
| Water | | 34.000 | 34.000 | trace | |
| P-XLY-01 | | | | | |
| Metha-01 | | | 800.00 | trace | 800.00 |
| Ethan-01 | | | | | |
| 1-PRO-01 | | | | | |
| Mass Frac | | | | | |
| 23BD | | 0.005 | 0.124 | 985PPM | |
| PG | | 0.973 | 0.117 | 0.978 | |
| 12BD | | 0.001 | 121PPM | 0.001 | |
| EG | | 0.020 | trace | 0.020 | |
| Water | | 0.001 | 0.031 | trace | |
| P-XLY-01 | | | | | |
| Metha-01 | | | 0.727 | trace | 1.000 |
| Ethan-01 | | | | | |
| 1-PRO-01 | | | | | |
| Mole Flow | lbmol/hr | | | | |
| 23BD | | 1.886 | 1.518 | 0.368 | |
| PG | | 434.744 | 1.696 | 433.048 | |
| 12BD | | 0.447 | 0.002 | 0.445 | |
| EG | | 10.956 | trace | 10.956 | |
| Water | | 1.887 | 1.887 | trace | |
| P-XLY-01 | | | | | |
| Metha-01 | | | 24.967 | trace | 24.967 |
| Ethan-01 | | | | | |
| 1-PRO-01 | | | | | |

FIGURE 3B

| PG RECTIFICATION | | | | | |
|---|---|---|---|---|---|
| Stream ID | | 1 | 2,3BDO | 4 | Ethanol |
| Temperature | F | 100.0 | 123.9 | 303.2 | 300.0 |
| Pressure | psi | 40.00 | 3.87 | 4.06 | 20.00 |
| Vapor Frac | | 0.000 | 0.000 | 0.000 | 1.000 |
| Mole Flow | lbmol/hr | 449.920 | 22.505 | 444.781 | 17.365 |
| Mass Flow | lb/hr | 34000.000 | 1100.004 | 33699.996 | 800.000 |
| Volume Flow | cuft/hr | 534.983 | 21.341 | 604.038 | 6982.865 |
| Enthalpy | MMBtu/hr | -93.784 | -2.986 | -88.767 | -1.685 |
| Mass Flow | lb/hr | | | | |
| 23BD | | 170.000 | 118.962 | 51.038 | |
| PG | | 33082.000 | 146.892 | 32953.108 | |
| 12BD | | 34.000 | 0.151 | 33.849 | |
| EG | | 680.000 | trace | 680.000 | |
| Water | | 34.000 | 35.000 | trace | |
| P-XLY-01 | | | | | |
| Metha-01 | | | | | |
| Ethan-01 | | | 800.00 | trace | 800.00 |
| 1-PRO-01 | | | | | |
| Mass Frac | | | | | |
| 23BD | | 0.005 | 0.108 | 0.002 | |
| PG | | 0.973 | 0.134 | 0.977 | |
| 12BD | | 0.001 | 137PPM | 0.001 | |
| EG | | 0.020 | trace | 0.020 | |
| Water | | 0.001 | 0.031 | trace | |
| P-XLY-01 | | | | | |
| Metha-01 | | | | | |
| Ethan-01 | | | 0.73 | trace | 1.00 |
| 1-PRO-01 | | | | | |
| Mole Flow | lbmol/hr | | | | |
| 23BD | | | 1.886 | 1.320 | 0.566 |
| PG | | | 434.744 | 1.930 | 432.814 |
| 12BD | | | 0.447 | 0.002 | 0.445 |
| EG | | | 10.956 | trace | 10.956 |
| Water | | | 1.887 | 1.887 | trace |
| P-XLY-01 | | | | | |
| Metha-01 | | | | | |
| Ethan-01 | | | | 17.365 | trace | 17.365 |
| 1-PRO-01 | | | | | |

FIGURE 4B

| PG RECTIFICATION ||||||
|---|---|---|---|---|---|
| Stream ID | | 1 | 2,3BDO | 4 | Propanol |
| Temperature | F | 100.0 | 150.8 | 303.2 | 300.0 |
| Pressure | psi | 40.00 | 3.87 | 4.06 | 20.00 |
| Vapor Frac | | 0.000 | 0.000 | 0.000 | 1.000 |
| Mole Flow | lbmol/hr | 449.920 | 18.479 | 444.754 | 13.312 |
| Mass Flow | lb/hr | 34000.000 | 1100.000 | 33700.000 | 800.000 |
| Volume Flow | cuft/hr | 534.983 | 21.609 | 604.044 | 5327.862 |
| Enthalpy | MMBtu/hr | -93.784 | -2.630 | -88.765 | -1.391 |
| Mass Flow | lb/hr | | | | |
| 23BD | | 170.000 | 105.684 | 64.316 | |
| PG | | 33082.000 | 160.152 | 32921.848 | |
| 12BD | | 34.000 | 0.165 | 33.835 | |
| EG | | 680.000 | trace | 680.000 | |
| Water | | 34.000 | 34.000 | trace | |
| P-XLY-01 | | | | | |
| Metha-01 | | | | | |
| Ethan-01 | | | | | |
| 1-PRO-01 | | | 800.000 | trace | 800.000 |
| Mass Frac | | | | | |
| 23BD | | 0.005 | 0.096 | 0.002 | |
| PG | | 0.973 | 0.146 | 0.977 | |
| 12BD | | 0.001 | 150PPM | 0.001 | |
| EG | | 0.020 | trace | 0.020 | |
| Water | | 0.001 | 0.031 | trace | |
| P-XLY-01 | | | | | |
| Metha-01 | | | | | |
| Ethan-01 | | | | | |
| 1-PRO-01 | | | 0.727 | trace | 1.000 |
| Mole Flow | lbmol/hr | | | | |
| 23BD | | 1.886 | 1.173 | 0.714 | |
| PG | | 434.744 | 2.105 | 432.640 | |
| 12BD | | 0.447 | 0.002 | 0.445 | |
| EG | | 10.956 | trace | 10.956 | |
| Water | | 1.887 | 1.887 | trace | |
| P-XLY-01 | | | | | |
| Metha-01 | | | | | |
| Ethan-01 | | | | | |
| 1-PRO-01 | | | 13.312 | trace | 13.312 |

FIGURE 5B

| PG RECTIFICATION | | | | | |
|---|---|---|---|---|---|
| Stream ID | | 1 | 2,3BDO | 4 | Xylene |
| Temperature | F | 100.0 | 132.5 | 303.2 | 300.0 |
| Pressure | psi | 40.00 | 3.87 | 4.06 | 20.00 |
| Vapor Frac | | 0.000 | 0.000 | 0.000 | 1.000 |
| Mole Flow | lbmol/hr | 449.920 | 12.759 | 444.697 | 7.535 |
| Mass Flow | lb/hr | 34000.000 | 1100.001 | 33699.999 | 800.000 |
| Volume Flow | cuft/hr | 534.983 | 20.100 | 604.055 | 17.237 |
| Enthalpy | MMBtu/hr | -93.784 | -1.000 | -88.761 | 0.004 |
| Mass Flow | lb/hr | | | | |
| 23BD | | 170.000 | 77.942 | 92.058 | |
| PG | | 33082.000 | 187.866 | 32894.134 | |
| 12BD | | 34.000 | 0.193 | 33.807 | |
| EG | | 680.000 | trace | 680.000 | |
| Water | | 34.000 | 34.000 | trace | |
| P-XLY-01 | | | 800.00 | trace | 800.00 |
| Metha-01 | | | | | |
| Ethan-01 | | | | | |
| 1-PRO-01 | | | | | |
| Mass Frac | | | | | |
| 23BD | | 0.005 | 0.071 | 0.003 | |
| PG | | 0.973 | 0.171 | 0.976 | |
| 12BD | | 0.001 | 176PPM | 0.001 | |
| EG | | 0.020 | trace | 0.020 | |
| Water | | 0.001 | 0.031 | trace | |
| P-XLY-01 | | | 0.727 | trace | 1.000 |
| Metha-01 | | | | | |
| Ethan-01 | | | | | |
| 1-PRO-01 | | | | | |
| Mole Flow | lbmol/hr | | | | |
| 23BD | | 1.886 | 0.865 | 1.021 | |
| PG | | 434.744 | 2.469 | 432.275 | |
| 12BD | | 0.447 | 0.003 | 0.444 | |
| EG | | 10.956 | trace | 10.956 | |
| Water | | 1.887 | 1.887 | trace | |
| P-XLY-01 | | | 7.535 | trace | 7.535 |
| Metha-01 | | | | | |
| Ethan-01 | | | | | |
| 1-PRO-01 | | | | | |

FIGURE 7B

PROCESSES FOR ISOLATING OR PURIFYING PROPYLENE GLYCOL, ETHYLENE GLYCOL AND PRODUCTS PRODUCED THEREFROM

CROSS-REFERENCE TO RELATED APPLICATIONS

The application claims the priority benefit under 35 U.S.C. §119(e) to U.S. Provisional Patent Application No. 60/854,987, filed Oct. 27, 2006, the contents of the entirety of which is incorporated by this reference.

TECHNICAL FIELD

This invention relates to a process for separating ethylene glycol or propylene glycol from mixtures containing the ethylene glycol or the propylene glycol and other polyols using polar compounds, as well as compositions obtained therefrom.

BACKGROUND

Propylene glycol and ethylene glycol are produced from petrochemical sources. Commercial production of propylene glycol involves the hydration of propylene oxide, which is made by the oxidation of propylene. The commercial production of ethylene glycol involves the hydration of ethylene oxide, made by the oxidation of ethylene. Propylene and ethylene are industrial by-products of gasoline manufacture, for example as by-products of fluid cracking of gas oils or steam cracking of hydrocarbons.

The world's supply of petroleum is being depleted at an increasing rate. Eventually, demand for petrochemical derived products will outstrip the supply of available petroleum. When this occurs, the market price of petroleum and, consequently, petroleum derived products will likely increase, making products derived from petroleum more expensive and less desirable. As the available supply of petroleum decreases, alternative sources and, in particular, renewable sources of comparable products will necessarily have to be developed. One potential renewable source of petroleum derived products is products derived from bio-based matter, such as agricultural and forestry products. Use of bio-based products may potentially counteract, at least in part, the problems associated with depletion of the petroleum supply.

In an effort to diminish dependence on petroleum products the United States government enacted the Farm Security and Rural Investment Act of 2002, section 9002 (7 U.S.C. 8102), hereinafter "FRISA", which requires federal agencies to purchase bio-based products for all items costing over $10,000. In response, the United States Department of Agriculture ("USDA") has developed Guidelines for Designating Bio-based Products for Federal Procurement (7 C.F.R. §2902) to implement FRISA, including the labeling of bio-based products with a "U.S.D.A. Certified Bio-based Product" label.

As used herein, the term "bio-derived" refers to a product derived from or synthesized by a renewable biological feedstock, such as, for example, an agricultural, forestry, plant, bacterial, or animal feedstock. As used herein, the term "bio-based" refers to a product that includes in whole or in significant part, biological products or renewable agricultural materials (including, but not limited to, plant, animal and marine materials) or forestry materials. As used herein, the term "petroleum derived" refers to a product derived from or synthesized from petroleum or a petrochemical feedstock. Propylene glycol that is produced by hydrogenolysis of a polyol, such as a carbohydrate, is referred to as bio-based propylene glycol.

FRISA has established certification requirements for determining bio-based content. These methods require the measurement of variations in isotopic abundance between bio-based products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-based products compared to petroleum products. Bio-based content of a product may be verified by ASTM International Radioisotope Standard Method D 6866. ASTM International Radioisotope Standard Method D 6866 determines bio-based content of a material based on the amount of bio-based carbon in the material or product as a percent of the weight (mass) of the total organic carbon in the material or product. Bio-derived and bio-based products will have a carbon isotope ratio characteristic of a biologically derived composition.

Biology offers an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. As the supply of easily extracted petrochemicals continues to be depleted, the economics of petrochemical production will likely force the cost of the petrochemicals and petroleum derived products to higher prices compared to bio-based products. In addition, companies may benefit from the marketing advantages associated with bio-derived products from renewable resources in the view of a public becoming more concerned with the supply of petrochemicals.

A number of commercial processes which produce polyols from complex mixtures of carbohydrates exist. These processes usually produce a homologous series of glycols. Some of the resulting polyols boil so close to one another that separation of the polyols by ordinary rectification is difficult. The relative volatility is so low that a large number of theoretical plates are required to produce high purity polyols.

In a process involving hydrocracking of higher carbohydrates, such as glucose, sorbitol or sucrose, the molecule is broken into fragments of lower molecular weight to form compounds which belong to the glycol or polyol family. For instance, U.S. Pat. No. 5,206,927 describes a homogeneous process for hydrocracking carbohydrates in the presence of soluble, transition metal catalyst with the production of lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. However, as is evident from Tables II and III in the disclosure of U.S. Pat. No. 5,206,927, about 2-7% of other polyol compounds are produced in the hydrocracking process.

U.S. Pat. Nos. 5,276,181 and 5,214,219 describe a process of hydrogenolysis of glycerol using copper and zinc catalyst in addition to sulfided ruthenium catalyst at a pressure over 2100 psi and temperature between 240-270° C. U.S. Pat. No. 5,616,817 describes a process of preparing 1,2 propanediol by catalytic hydrogenolysis of glycerol at elevated temperature and pressure using a catalyst comprising the metals cobalt, copper, manganese and molybdenum. German patent DE 541362 describes the hydrogenolysis of glycerol with a Nickel catalyst, while U.S. Pat. No. 4,476,331 describes a two stage method of hydrocracking carbohydrates (for example glucose), wherein a modified ruthenium catalyst is used for hydrocracking sorbitol to produce glycerol derivatives. European Patent applications EP-A-0 523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Persoa & Tundo (Ind. Eng. Chem. Res. 2005, 8535-8537) describe a process for converting glycerol to 1,2-propanediol by heating under low hydrogen pressure in presence of Raney nickel and a liquid phosphonium salt. Selectivities toward 1,2-Propanediol as high as 93% were reported, but required using a pure glycerol and long reaction times (20 hrs). Crabtree et al. (Hydrocarbon processing February 2006 pp 87-92) describe a phosphine/precious metal salt catalyst that permit a homogenous catalyst system for converting glycerol into 1,2-PD. However, low selectivity (20-30%) was reported. Other reports indicate use of Raney Copper (Montassier et al. Bull. Soc. Chim. Fr. 2 1989 148; Stud. Surf. Sci. Catal. 41 1988 165), copper on carbon (Montassier et al. J. Appl. Catal. A 121 1995 231)), copper-platinum and copper ruthenium (Montassier et al. J. Mol. Catal. 70 1991 65). Other homogenous catalyst systems such as tungsten and Group VIII metal-containing catalyst compositions have been also tried (U.S. Pat. No. 4,642,394). Miyazawa et al. (J. Catal. 240 2006 213-221) & Kusunoki et al (Catal. Comm. 6 2005 645-649) describe a Ru/C and ion exchange resin for conversion of glycerol in aqueous solution. Again their process however, results in low conversions of glycerol (0.9-12.9%).

One of the problems of producing glycerol derivatives by hydrogenolysis of glycerol is that other diol compounds are formed which reduce the purity of the desired component. For instance, in hydrocracking of higher carbohydrates such as, for example, sorbitol to produce propylene glycol, typically 3-5% by weight of 2,3-butanediol is produced in addition to 1,2 butanediol, ethylene glycol and 1,3-butanediol. These products are referred to as "polyols" or "polyhydric alcohols". The boiling points of these components as shown in Table 1 are very close to one another such that in a rectification column, either under atmospheric, reduced pressure or at an elevated pressure, the separation of substantially pure propylene glycol from these other polyhydric alcohols is difficult to be attained.

TABLE 1

Polyols produced by Hydrocracking of Sorbitol

| Polyol | Weight Percent | Boiling Point, ° C. |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |

TABLE 1-continued

Polyols produced by Hydrocracking of Sorbitol

| Polyol | Weight Percent | Boiling Point, ° C. |
|---|---|---|
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerin | 38.8 | 290 |
| 1,2,4-Butanetriol | 4.8 | 190/18 mm |
| | 100.00 | |

The differences in volatility of propylene glycol compared to 2,3-butanediol or 1,2 butanediol are very small. As shown in Tables 2 and 3, the number of plates required to achieve 99% purity is very large, requiring the use of very tall distillation columns (55 trays for 2,3-Butanediol and 88 trays for 1,2-Butanediol) and high energy inputs.

TABLE 2

Theoretical and Actual Plates Required vs. Relative volatility for Separation of Propylene Glycol and 2,3-Butanediol.

| Relative Volatility | Theoretical Plates | Actual Plates, 75% Efficiency |
|---|---|---|
| 1.25 | 41 | 55 |
| 1.35 | 31 | 42 |
| 1.45 | 25 | 34 |
| 1.50 | 23 | 31 |
| 1.70 | 18 | 24 |

TABLE 3

Theoretical and Actual Plates Required vs. Relative volatility for Separation of Propylene Glycol and 1,2-Butanediol.

| Relative Volatility | Theoretical Plates | Actual Plates, 75% Efficiency |
|---|---|---|
| 1.15 | 66 | 88 |
| 1.5 | 23 | 31 |
| 2.0 | 14 | 19 |
| 3.0 | 9 | 12 |
| 3.5 | 8 | 11 |

Several reports in the literature describe efforts for azeotropically separating glycerol derivatives such as 2,3 butanediol from propylene glycol. For instance, U.S. Pat. No. 4,935,102 describes a method for using an azeotrope forming agent such as propylene glycol isobutyl ether, tetrahydro furfuryl alcohol, N,N-dimethylacetamide, ethylene glycol diethyl ether, diethylene glycol diethyl ether, 2-methoxyethyl ether, ethylene glycol n-butyl ether, diacetone alcohol and ethyl n-butyl ketone. In U.S. Pat. No. 5,423,955, the azeotrope forming agent consists of a material selected from the group consisting of toluene, ethyl benzene, o-xylene, p-xylene, cumene, m-diisopropyl benzene, m-diethyl benzene, mesitylene, p-cymene, hexane, cyclohexane, methyl cyclohexane, heptane, 3-methyl pentane, octane, decane, 2,3,4-trimethyl pentane, dipentene, decalin, dicyclopentadiene, alpha-phellandrene, limonene, hemimellitene, myrcene, terpinolene, p-mentha-1,5-diene, beta-pinene, 3-carene, 1-heptene, cyclopentane, pentane, o-diethyl benzene, 2,2-dimethyl butane and 2-methyl butane. The azeotrope forming agents described in U.S. Pat. Nos. 4,935,102 and 5,423,955 may be characterized by their Hansen solubility parameters (Table 4).

TABLE 4

Azeotropic agents used for separation of 2,3-Butanediol from propylene glycol (U.S. Pat. No. 4,935,102).

| Azeotropic agent | Hansen p | Hansen h |
|---|---|---|
| Propylene glycol isobutyl ether | 5.42 | 12.52 |
| Tetrahydrofurfuryl alcohol | 10.46 | 10.96 |
| N,N-dimethylacetamide | 11.47 | 10.23 |
| Toluene | 0.75 | 1.98 |
| Ethyl benzene | 0.65 | 1.85 |
| p-Xylene | 0.91 | 1.84 |
| m-Xylene | 0.91 | 1.84 |
| o-Xylene | 0.91 | 1.84 |
| Cumene | 0.58 | 1.74 |
| Mesitylene | 0.98 | 1.7 |
| Ethylene glycol diethyl ether | 9.19 | 14.3 |
| Diethylene glycol diethyl ether | 9.22 | 12.33 |
| 2-Methoxyethyl ether | 1.81 | 7.41 |
| Ethylene glycol-n-butyl ether | 5.13 | 12.27 |
| Diacetone alcohol | 8.17 | 10.76 |
| 3-heptanone | 5.28 | 3.93 |

Azeotropic distillation using organic solvents as an azeotropic agent has also proven useful for azeotropically separating ethylene glycol from 1,2 butanediol (Table 5).

TABLE 5

Azeotropic agents used for separation of 1,2-Butanediol from ethylene glycol (U.S. Pat. No. 5,432,955).

| Azeotropic agent | Hansen p | Hansen h |
|---|---|---|
| 3-Heptanone | 5.28 | 3.93 |
| Cyclohexanone | 3.13 | 5.08 |
| Diisobutyl ketone | 4.9 | 3.79 |
| Methyl isoamyl ketone | 6.03 | 4.2 |
| Isobutyl heptyl ketone | 3.76 | 3.31 |
| 2-Methoxyethyl ether | 1.81 | 7.41 |
| 2,6-Dimethyl-4-heptanone | 4.90 | 3.79 |
| p-Xylene | 0.91 | 1.84 |
| m-Xylene | 0.91 | 1.84 |
| o-Xylene | 0.91 | 1.84 |
| Ethyl benzene | 0.65 | 1.85 |
| Cumene | 0.58 | 1.74 |
| Mesitylene | 0.98 | 1.7 |

The azeotropic agents used in U.S. Pat. Nos. 4,935,102 and 5,432,955 can be described by Hansen solubility parameters, which are described in detail in "Hansen Solubility Parameters: A User's Handbook," by Charles M. Hansen (CRC Press, 1999), which is incorporated by reference in its entirety. Hansen solubility parameters can be calculated using the program "Molecular Modeling Pro Plus (version 6.0.6, Norgwyn Montgomery Software Inc, available from ChemSW, Inc) based on values published in the "Handbook of Solubility Parameters and Other Parameters" by Allen F. M. Barton (CRC Press, 1983) for solvents obtained experimentally by Hansen. The Hansen "h" (hydrogen bonding) values at 25° C. and Hansen "p" (polarity) values ° C. listed in Tables 4 and 5 were calculated in this manner.

Thus, a need exists for an economical process of separating polyethylene glycol and/or ethylene glycol from other polyhydric alcohols.

SUMMARY OF THE INVENTION

In one embodiment, a process for isolating or purifying bio-based propylene glycol, bio-based ethylene glycol or a combination thereof comprises placing the bio-based propylene glycol, the bio-based ethylene glycol or the combination thereof, and a polar solvent in an apparatus. The bio-based propylene glycol, the bio-based ethylene glycol or the combination thereof, and the polar solvent are distilled in the apparatus. The process further includes collecting the bio-based propylene glycol, the bio-based ethylene glycol or the combination thereof.

In another embodiment, an isolated or purified bio-based propylene glycol, an isolated or purified biobased ethylene glycol, or a combination thereof has less than 0.2 weight percent of 1,2-butanediol, 2,3-butanediol or a combination thereof.

In yet another embodiment, a system for removing butanediols from bio-based propylene glycol, bio-based ethylene glycol or a combination thereof includes a first conduit comprising the bio-based propylene glycol, the bio-based ethylene glycol, or the combination thereof. The system further comprises an apparatus configured for distilling a mixture the bio-based propylene glycol, the bio-based ethylene glycol or the combination thereof, and the butanediols. The system also includes a second conduit comprising an isolated or purified bio-based propylene glycol, an isolated or purified bio-based ethylene glycol or a combination thereof, and a third conduit comprising the butanediols.

DESCRIPTION OF THE DRAWINGS

FIGS. 1A and 1B illustrate the conditions of one embodiment of a process of the present invention, as well as the results obtained therefrom.

FIGS. 2A and 2B depict the conditions of another embodiment of a process of the present invention, as well as the results obtained therefrom.

FIGS. 3A and 3B present the conditions of an additional embodiment of a process of the present invention, as well as the results obtained therefrom.

FIGS. 4A and 4B illustrate the conditions of a further embodiment of a process of the present invention, as well as the results obtained therefrom.

FIGS. 5A and 5B describe the conditions of one embodiment of a process of the present invention, as well as the results obtained therefrom.

FIGS. 7A and 7B depict the conditions of yet another embodiment of a process of the present invention, as well as the results obtained therefrom.

DETAILED DESCRIPTION

Figure 1A:
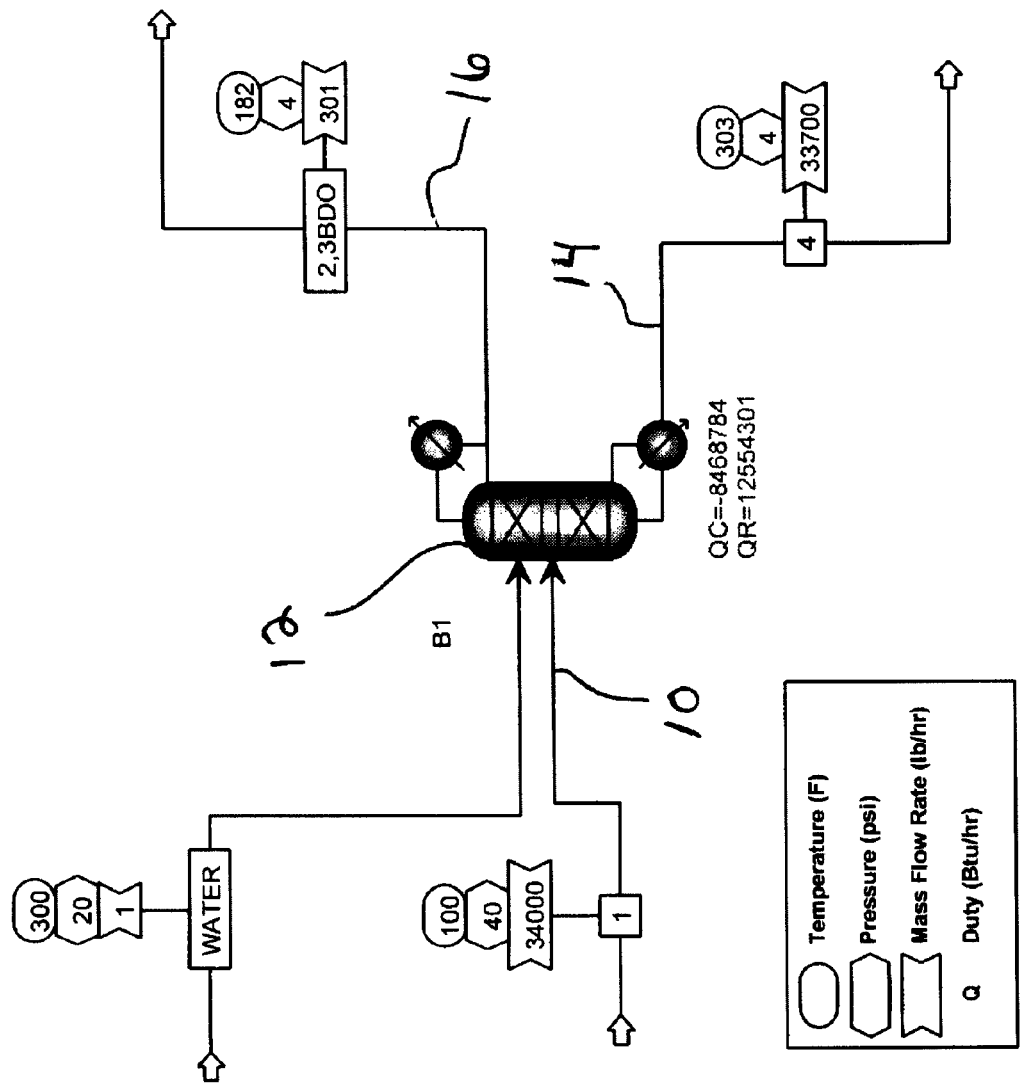

In each of its various embodiments, the present invention fulfills this need. In one embodiment, this invention describes a method to improve the relative volatility of propylene glycol over other polyols without the use of an azeotrope forming agent, which are typically organic compounds, and are difficult to process and handle due to environmental regulations. In one embodiment, this invention describes the use of polar solvents that increase the separation efficiency of propylene glycol and/or ethylene glycol from other polyols. Polar solvents that may be used include, but are not limited to, a primary alcohol which is also produced by some of the hydrocracking routes employed to produce such polyols or some of the hydrogenolysis routes employed to convert glycerol into polyols. With the aid of such polar solvents, the undesirable species that reduce the purity of propylene glycol may be effectively removed.

In another embodiment, the present disclosure teaches a method where purified propylene glycol or purified ethylene glycol may be obtained from a mixture containing propylene glycol, ethylene glycol and butanediols, such as a mixture obtained by the hydrocracking or hydrogenolysis of a carbohydrate or polyol, such as glycerol. In one embodiment, a compound which does not form an azeotrope is mixed with the product of a hydrocracking or hydrogenolysis reaction and extractive distillation is carried out. Extractive distillation is defined by Wikipedia (access date Oct. 20, 2006 at http://en.wikipedia.org/wiki/Extractive_Distillation) as follows:

Extractive distillation includes a distillation in the presence of a miscible, high boiling, relatively non-volatile component, i.e., the solvent, that forms no azeotrope with the other components in the mixture. Extractive distillation is used for mixtures having a low value of relative volatility, nearing unity. Mixtures having a low relative volatility cannot be separated by simple distillation because the volatility of both the components in the mixture is nearly the same causing the components to evaporate at nearly the same temperature to a similar extent, thus reducing the chances of separating the components by condensation.

The method of extractive distillation uses a polar solvent, which is generally nonvolatile, has a high boiling point and is miscible with the mixture, but does not form an azeotropic mixture. The polar solvent interacts differently with the components of the mixture and causes the relative volatilities of the components to change, thus enabling the mixture to be separated through distillation. In such distillation, the component with the greater volatility separates out as the top product. The bottom product includes the lower volatility product. The polar solvent can be separated from the fraction in which the polar solvent is present because the polar solvent does not form an azeotrope. The polar solvent can be separated from such fraction by any of the methods available in the art including, without limitation, a secondary distillation or membrane separation.

In various embodiments, extractive distillation agents (i.e., polar solvents) useful in the present disclosure have Hansen polarity (P) values of greater than about 12 (delta/sqr(MPa)) and Hansen hydrogen bonding (H) values of greater than about 15 (delta/sqr(MPa)). The Hansen P and H values, respectively, for the following distillation agents are: water, 16 and 42.3 (delta/sqr(MPa)), respectively; for ethanol, 8.8 and 19.4; for methanol, 12.29 and 22.31 for methanol. Thus, the polar solvents which may be used have a Hansen P value in excess of 12 (delta/sqr(MPa)) and a Hansen H value in excess of 15 (delta/sqr(MPa)). In another embodiment, as ethanol is widely regarded as a polar solvent, polar solvents that may be used comprise compounds having either a Hansen P value in excess of 12 (delta/sqr(MPa)) or a Hansen H value in excess of 15 (delta/sqr(MPa)), wherein the ratio of P value to H value is less than 0.5.

In one embodiment, a method of using polar solvents such as alcohols that do not act as an azeotrope forming agent and aid in the removal of 1,2-butanediol and 2,3-butanediol from propylene glycol and/or ethylene glycol are described. In another embodiment, a polar solvent such as water may be used.

The bio-based propylene glycol, the bio-based ethylene glycol or the combination thereof obtained by the processes of the present invention may be subjected to further purification or isolation techniques in order to get a purity of at least 95%. In a further embodiment, the purity may be obtained to at least 99.5% or even 99.7% depending on the desired use of the bio-based propylene glycol, the bio-based ethylene glycol or the combination thereof.

Propylene glycol produced by the embodiments of this process is referred to as "bio-based" propylene glycol. Propylene glycol produced as such finds many uses. Some of these include, without limitation, use as a solvent for aromatics in the flavor-concentrate industry; a wetting agent for natural gums; an ingredient in the compounding of citrus and other emulsified flavors; a solvent in elixirs and pharmaceutical preparations; a solvent and coupling agent in the formulation of sunscreen lotion shampoos, shaving creams and other similar products; an emulsifier in cosmetic and pharmaceutical creams; an ingredient for low-temperature heat-transfer fluids, involving indirect food contacts, such as brewing and dairy uses, as well as refrigerated grocery display cases; a humectant, preservative, and stabilizer in semi-moist pet food (with the exception of cat food), bakery goods, food flavorings and salad dressings; use as a dust suppression agent; solvents and compatibilizers for the many dyes, resins and inks used in modern high-speed printing presses; surface lubricant in metal part manufacture; as a raw material for dipropylene glycol phthalate; a plasticizer for polyvinyl chloride (PVC) resins; for use in the natural gas processing industry; and to provide freeze-thaw protection in various wax products to help prevent damaged caused by freezing. Propylene glycol is also used as the starting material for the synthesis of propylene glycol esters with sorbitol and/or fatty acids. Such uses are not limited or all inclusive and may be readily developed by those skilled in the art.

Various embodiments of the present disclosure relate to a bio-based replacement for propylene glycol and ethylene glycol derived from petrochemical sources. In particular, bio-based propylene glycol and bio-based ethylene glycol can be produced by hydrogenolysis of polyols derived from biological sources (i.e., bio-derived). Various applications for the bio-based hydrogenolysis product mixture are also disclosed. The product mixture from the hydrogenolysis of bio-derived polyols and the products produced therefrom may be differentiated from petroleum derived products, for example, by their carbon isotope ratios using ASTM International Radioisotope Standard Method D 6866. Products produced and present in the product mixture of the hydrogenolysis product from a bio-derived polyol feedstock may have a bio-based carbon isotope ratio ranging from 50% to 100. As used herein the term "bio-based carbon isotope ratio" includes a composition or a component of a composition having a carbon isotope ratio, as determined, for example, by ASTM International Radioisotope Standard Method D 6866, the disclosure of which is incorporated by reference herein in its entirety, that is indicative of a composition including, in whole or in significant part, of biological products or renewable agricultural materials (including plant, animal and marine materials) or forestry materials (Method ASTM 6866).

Other than in the operating examples, or where otherwise indicated, all numbers expressing quantities of ingredients, reaction conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, may contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

It is understood, however, that the invention embraces numerous embodiments, which may be accomplished by combining any of the different features and aspects described herein any combination that one of ordinary skill in the art would find useful.

EXAMPLES

Example 1

Figure 2A:
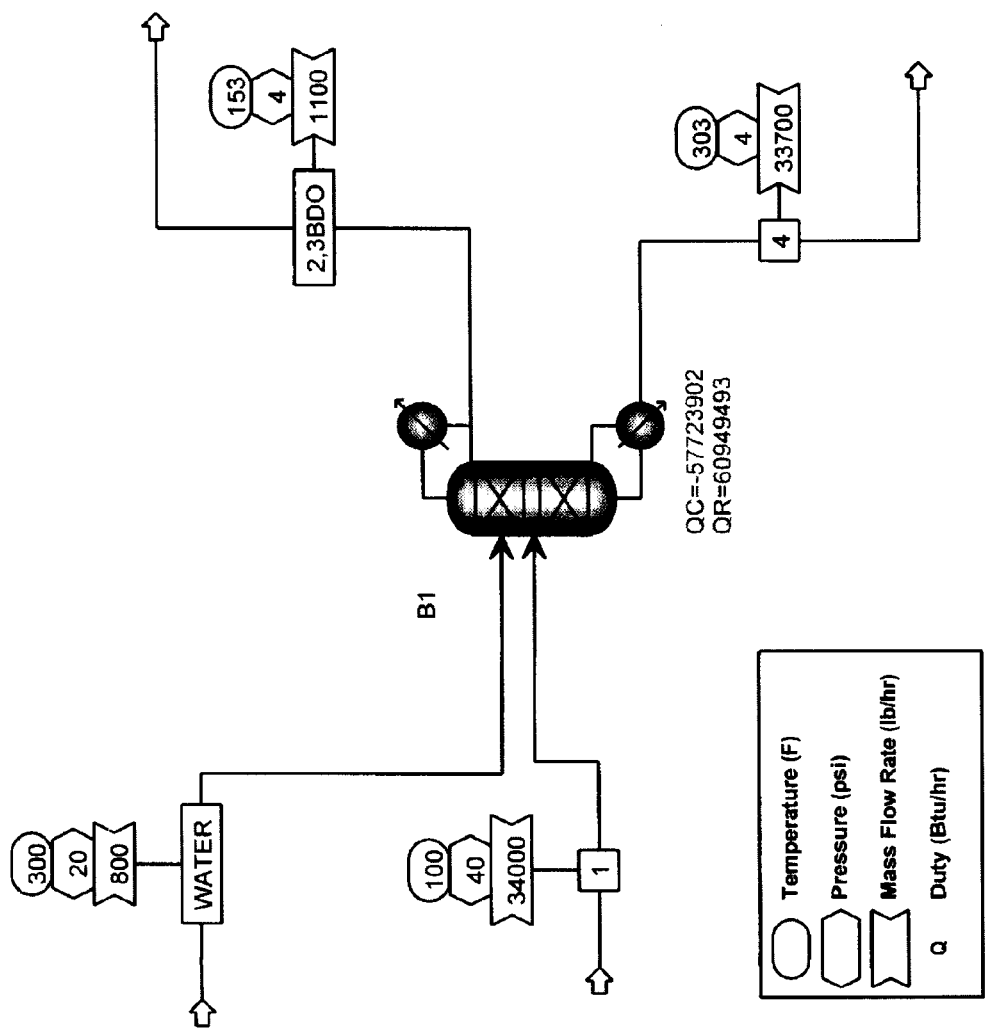

A series of studies were conducted in a 2000 ml high-pressure Stainless Steel 316 reactor. A solid catalyst similar to the "G" catalyst disclosed in U.S. Pat. No. 6,479,713 or the "HC-1" catalyst available from Sud Chemie (Louisville, Ky.) was loaded in the reactor to a final volume of 1000 ml of catalyst. The reactor was jacketed with a hot oil bath to provide for the elevated temperature for reactions and the feed and hydrogen lines were also preheated to the reactor temperature. A solution of a bio-based, substantially pure, 40% USP grade glycerol was fed through the catalyst bed at LHSV ranging from 0.5 $hr^{-1}$ to 2.5 $hr^{-1}$. Hydrogen was supplied at 1200-1600 psi and was also re-circulated through the reactor at a hydrogen to glycerol feed molar ratio of 5:1. In other embodiments, the hydrogen to glycerol feed molar ratio may be between 1:1 to 10:1. Tables 5A and 5B in FIGS. 2A and 2B describe the results with hydrogenolysis of 40% USP grade glycerol feed. Between 47.7-96.4% of the glycerol was converted and between 36.3-55.4% of propylene glycol was produced. In addition to propylene glycol, the hydrogenolysis reaction produced 0.04-2.31% unwanted BDOs, which may present a problem for recovery of pure propylene glycol (Table 6). The BDOs were measured using a known gas chromatography analysis method.

TABLE 6

Hydrogenolysis of 40% USP Glycerol Feed using a solid phase catalyst.

| Run # | Temperature, °C. | | | $H_2$ Press. (psi) | NaOH (%) w/w | LHSV | Conversion (%) | PG Yield (%) | PG Selectivity (%) | Butanediol's (g/100 g) | | |
|---|---|---|---|---|---|---|---|---|---|---|---|---|
| | Top | Mid | Bottom | | | | | | | 1-2 BDO | 1-3 BDO | 2-3 BDO |
| 248 | 183 | 191 | 199 | 1600 | 1 | 2.3 | 47.7 | 36.3 | 92.1 | 0 | 0 | 0.04 |
| 249 | 184 | 191 | 199 | 1600 | 1 | 1.8 | 56.7 | 42.4 | 90.8 | 0 | 0 | 0.05 |
| 250 | 185 | 193 | 199 | 1600 | 1 | 1.5 | 63.3 | 47.3 | 90.7 | 0.02 | 0 | 0.09 |
| 205 | 178 | 190 | 198 | 1200 | 1.2 | 1.8 | 50 | 38 | 94 | 0.03 | 0 | 0.16 |
| 257 | 184 | 195 | 206 | 1600 | 1 | 1.8 | 59.2 | 45.3 | 92.6 | 0 | 0.02 | 0.05 |
| 264 | 178 | 190 | 196 | 1600 | 1.9 | 1.6 | 59.3 | 44.3 | 90.3 | 0 | 0.01 | 0.05 |
| 261 | 184 | 194 | 200 | 1600 | 1 | 1.5 | 59.4 | 44.4 | 90.4 | 0 | 0 | 0.05 |
| 242 | 185 | 194 | 205 | 1600 | 0.7 | 1.8 | 65.2 | 33.2 | 92.2 | 0.05 | 0 | 0.26 |
| 199 | 154 | 177 | 194 | 1200 | 1.2 | 1.8 | 67 | 47.9 | 86.6 | 0.07 | 0 | 0.38 |
| 262 | 183 | 196 | 202 | 1600 | 1.5 | 1.5 | 67.2 | 49.8 | 89.6 | 0 | 0 | 0.08 |
| 263 | 181 | 193 | 199 | 1600 | 1.9 | 1.6 | 68.8 | 50.6 | 89.1 | 0 | 0.01 | 0.1 |
| 180 | 178 | 191 | 202 | 1200 | 1.1 | 1.0 | 76.7 | 51 | 80.7 | 0.1 | 0 | 0.57 |
| 256 | 189 | 206 | 217 | 1600 | 0.8 | 1.8 | 77.1 | 55.9 | 87.6 | 0 | 0.04 | 0.17 |
| 254 | 193 | 211 | 223 | 1600 | 1 | 1.8 | 81.2 | 60.8 | 90.6 | 0 | 0.06 | 0.29 |
| 255 | 191 | 209 | 221 | 1600 | 0.8 | 1.8 | 86.2 | 52.4 | 73.6 | 0 | 0.06 | 0.29 |
| 228 | 193 | 228 | 229 | 1600 | 1.4 | 1.8 | 93.1 | 64 | 83.2 | 0.14 | 0 | 0.69 |
| 240 | 188 | 212 | 226 | 1600 | 1.3 | 1.8 | 93 | 63.1 | 82.2 | 0.19 | 0 | 1.05 |
| 164 | 183 | 203 | 207 | 1200 | 1.1 | 1 | 94.6 | 68.6 | 87.7 | 0.12 | 0 | 0.61 |
| 166 | 188 | 211 | 216 | 1200 | 1.5 | 1 | 95.4 | 47.7 | 60.7 | 0.12 | 0 | 0.81 |
| 191 | 165 | 205 | 227 | 1200 | 1.6 | 1.8 | 96.4 | 55.4 | 69.6 | 0.23 | 0 | 1.65 |

The exemplary embodiments of the processes of Examples 2-7 were modeled using the ASPEN Plus™ software version 12.0, available from Aspen Technologies, Inc. (Cambridge, Mass.).

Example 2

Extractive distillation of a feed mixture of propylene glycol, ethylene glycol, 1,2-butanediol, 2,3-butanediol and trace amounts of water to be distilled in a stainless steel structured packed column under reflux conditions was simulated using ASPEN Plus™ software version 12.0, available from Aspen Technologies, Inc. (Cambridge, Mass.). In these Examples, the components and amounts of the feed mixture that were used are representative of a product produced that may be produced by the hydrogenolysis process of Example 1. However, it will be apparent by those of ordinary skill in the art that the processes and conditions described herein may be varied and optimized depending on the feed stock used. As shown in FIG. 1B, overheads were predicted to contain 0.758 mole fraction of propylene glycol and 0.125 mole fraction of 2,3-Butanediol. A loss of propylene glycol in the overhead fraction with 2,3-butanediol was predicted by the model.

FIG. 1A also illustrates one embodiment of a system for removing butanediols from propylene glycol, ethylene glycol or a combination thereof of the present invention. A conduit 10 transports the propylene glycol, the ethylene glycol or the combination thereof to an apparatus 12 configured to distill a mixture of the propylene glycol, the ethylene glycol or the combination thereof, and the butanediols. A conduit 16 transports the butanediols that have been removed from the mixture. The conduit 16 is in fluid communication with the apparatus 12. Another conduit 14 transports the isolated or purified propylene glycol, ethylene glycol or combination thereof away from the apparatus 12.

Figure 8:
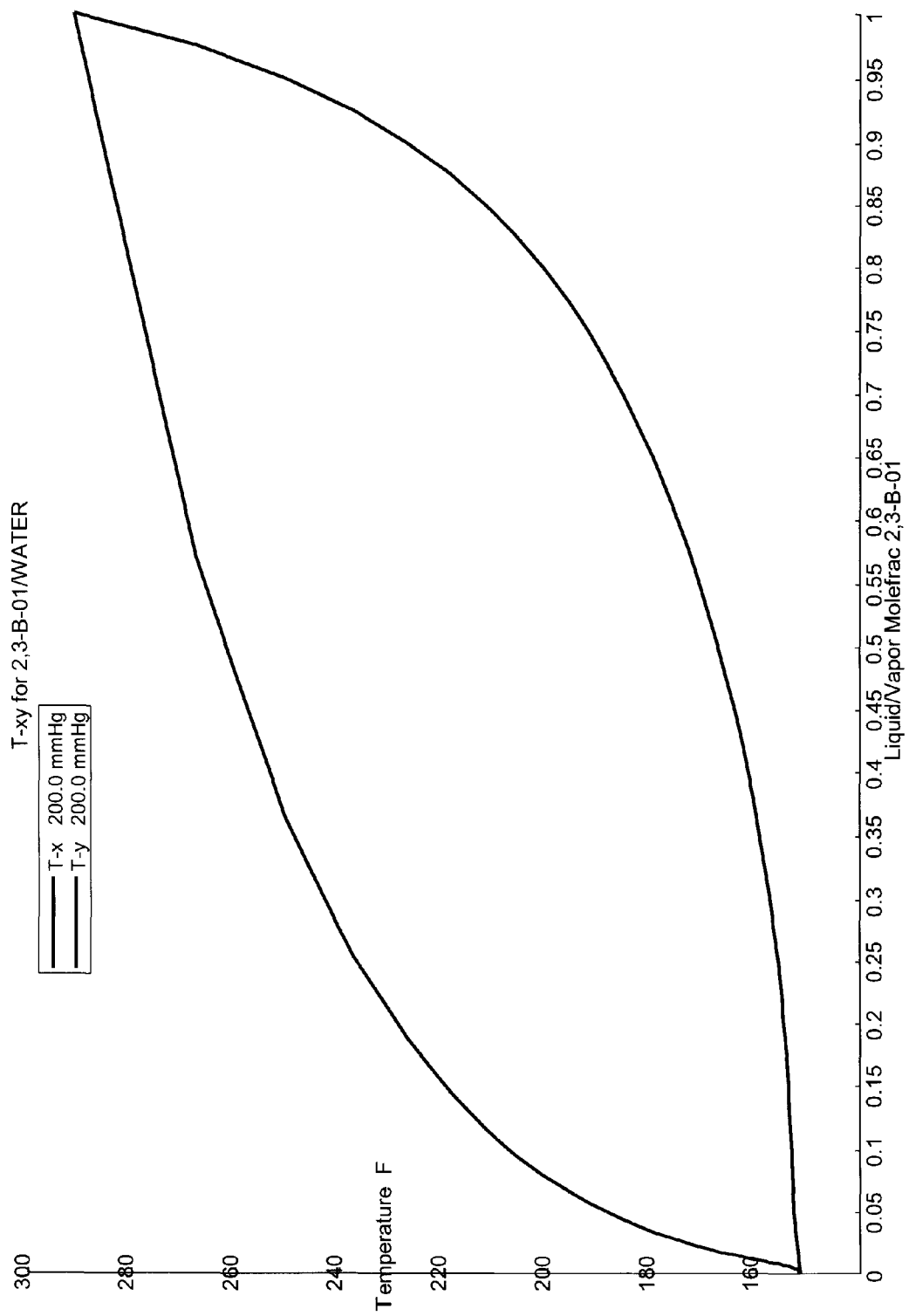
FIG. 8 illustrates a graph showing the lack of an azeotrope between water and 2,3-butanediol in one embodiment of the present invention.

Extractive distillation of a feed mixture of propylene glycol, ethylene glycol, 1,2-Butanediol, 2,3-Butanediol and trace amounts of water mixed with the polar solvent, water, to form a solution containing approximately 10% water to be distilled in a stainless steel structured packed column under reflux conditions was simulated substantially the same as described in example 2. As shown in FIG. 2B, overheads were predicted to contain 0.092 mole fraction of propylene glycol and 0.15 mole fraction of 2,3-Butanediol. Addition of the polar solvent (i.e., water) was expected to reduce the overhead loss of propylene glycol from 0.758 mole fraction (example 2) to 0.092 mole fraction. The still pot bottoms (undistilled residue) were predicted to contain propylene glycol, 1,2-butanediol and ethylene glycol recovered with trace amounts of water, and 2,3-butanediol. FIG. 8 shows the lack of an azeotrope between water and 2,3-butanediol.

Figure 3A:
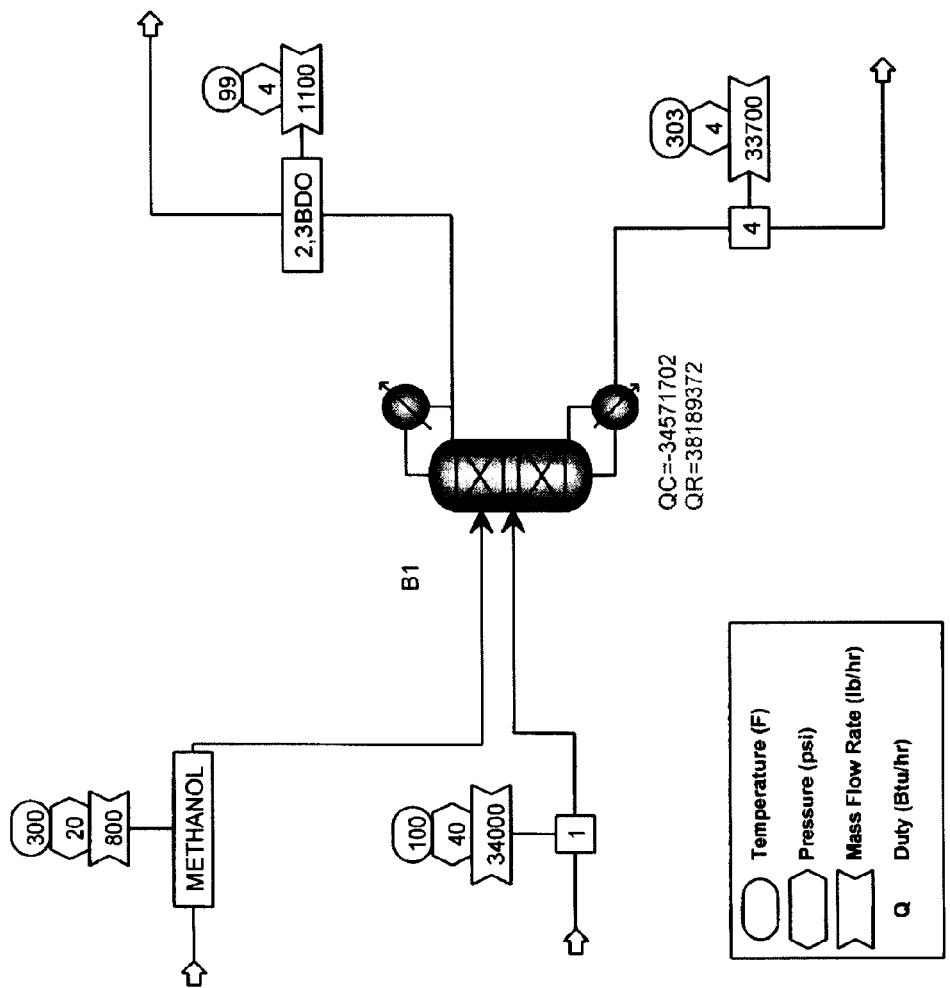
Figure 9:
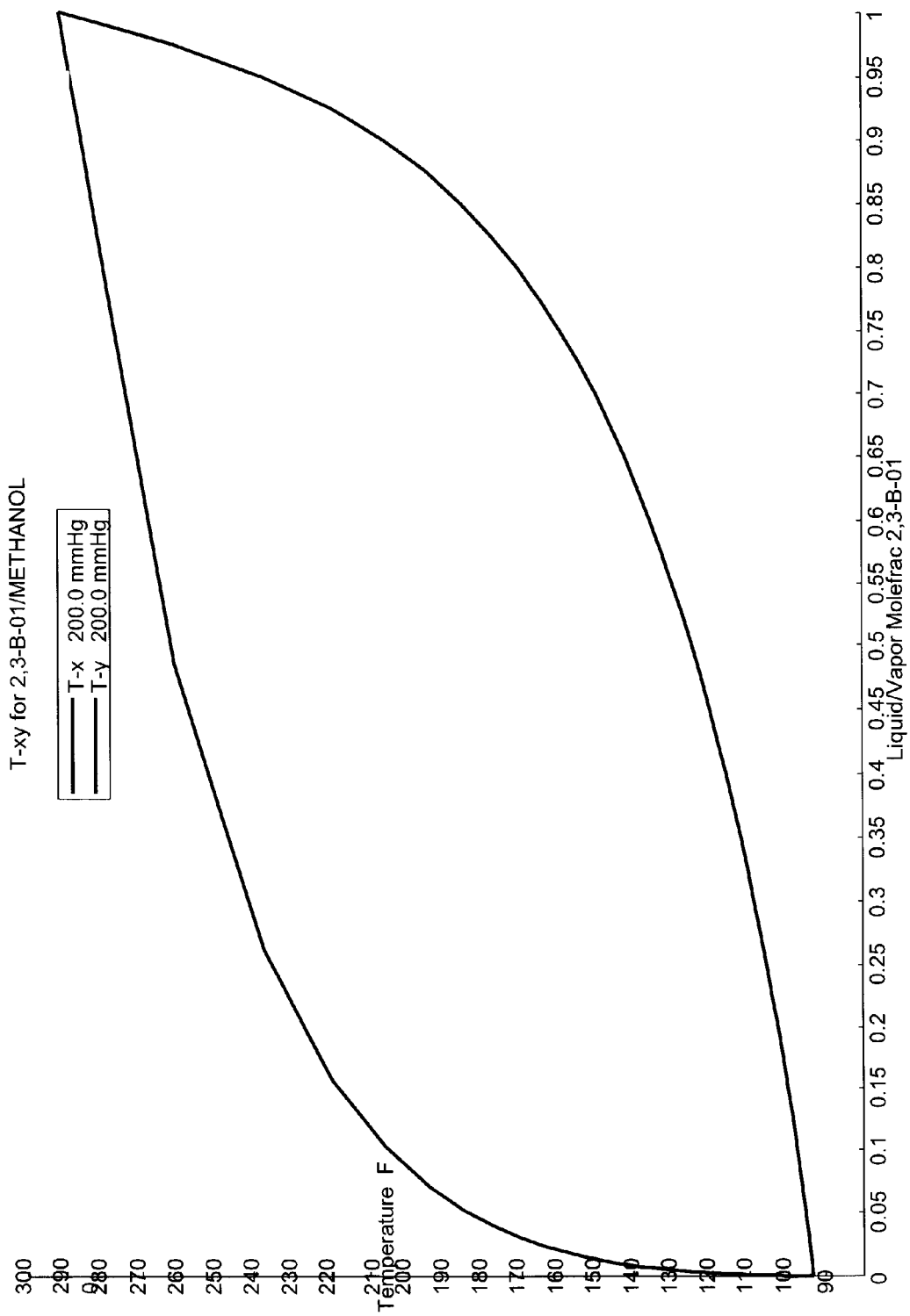
FIG. 9 depicts a graph indicating the lack of an azeotrope between methanol and 2,3-butanediol in one embodiment of the present invention.

Extractive distillation of a feed mixture of propylene glycol, ethylene glycol, 1,2-butanediol, 2,3-butanediol and trace amounts of water mixed with the polar solvent, methanol, to form a solution containing approximately 5% methanol to be distilled in a stainless steel structured packed column under reflux conditions was simulated substantially as described in example 2. As shown in FIG. 3B, overheads were predicted to contain 0.117 mole fraction of propylene glycol and 0.124 mole fraction of 2,3-Butanediol. Hence addition of a polar solvent like water was expected to reduce the overhead loss of propylene glycol from 0.758 mole fraction (example 2) to 0.117 mole fractions. The still pot bottoms (undistilled residue) were predicted to contain propylene glycol, 1,2-butanediol and ethylene glycol recovered with trace amounts of water, and 2,3-butanediol. FIG. 9 shows the lack of an azeotrope between methanol and 2,3-butanediol (2,3-B-01).

Figure 4A:
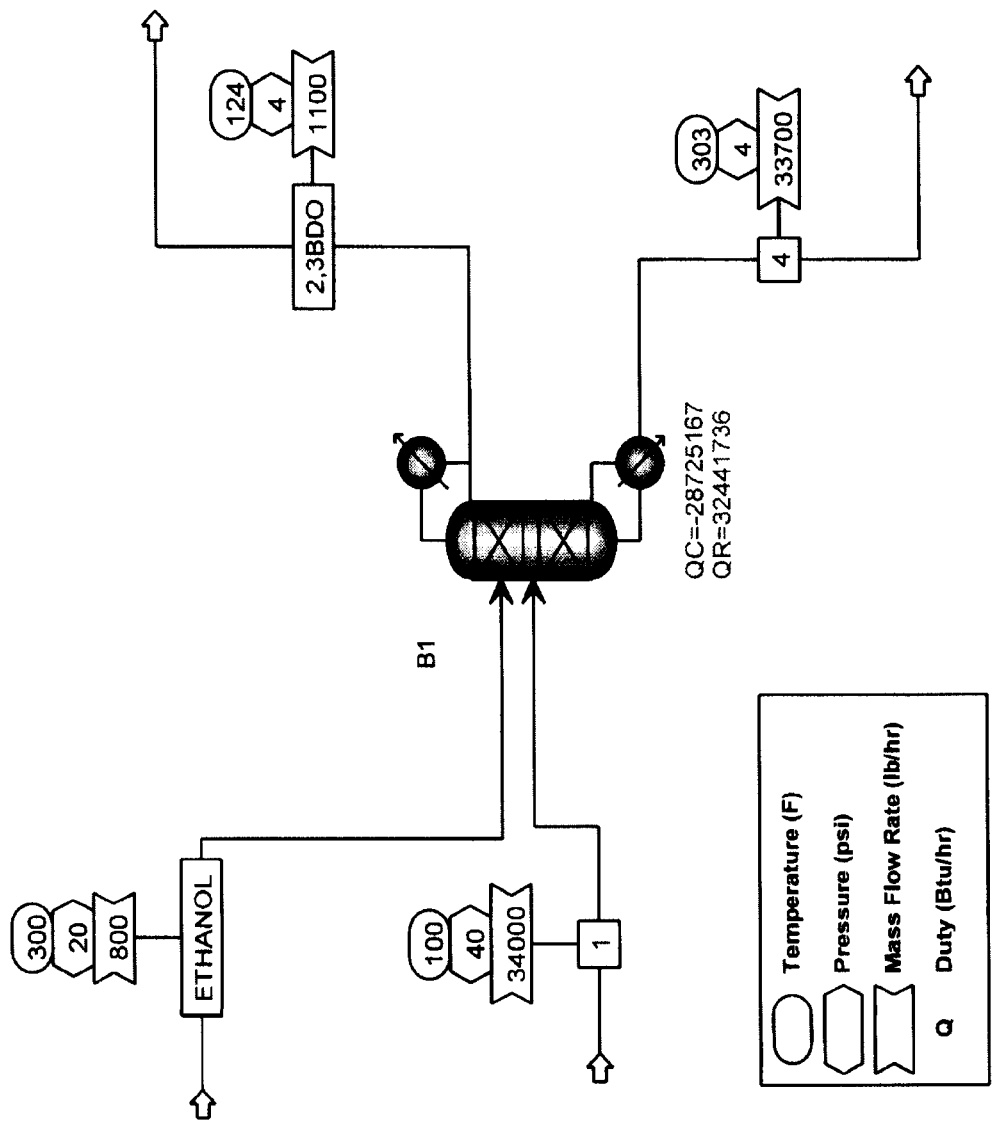
Figure 10:
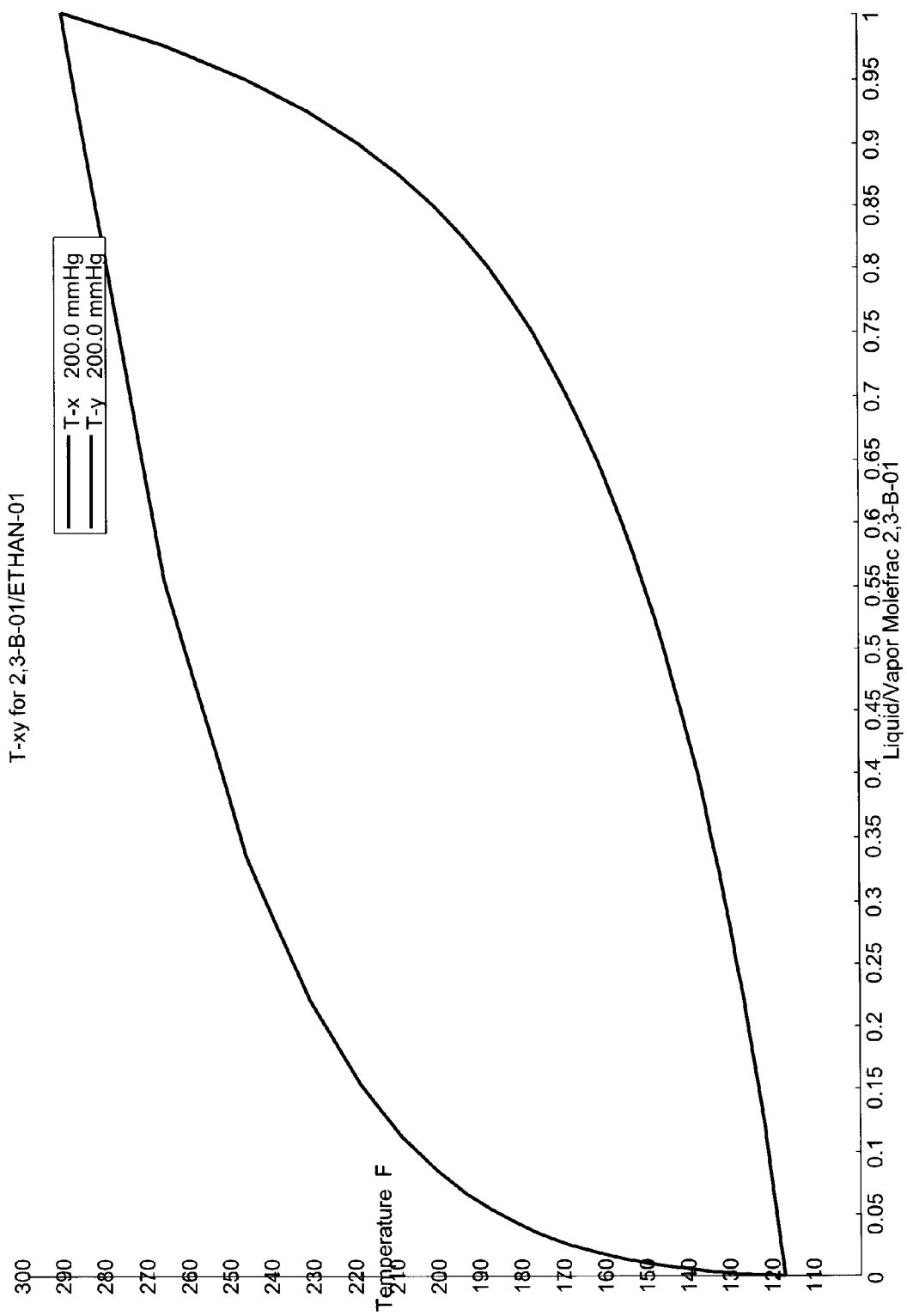
FIG. 10 illustrates a graph showing the lack of an azeotrope between ethanol and 2,3-butanediol in one embodiment of the present invention.

Extractive distillation of a feed mixture of propylene glycol, ethylene glycol, 1,2-butanediol, 2,3-butanediol and trace amounts of water mixed with the polar solvent, ethanol, to form a solution containing approximately 3.2% ethanol to be distilled in a stainless steel structured packed column under reflux conditions was simulated substantially as described in example 2. As shown in FIG. 4B, the simulation predicted that the overheads would contain 0.134 mole fraction of propylene glycol and 0.108 mole fraction of 2,3-Butanediol. Hence, addition of a polar solvent like water is expected to reduce the overhead loss of propylene glycol from 0.758 mole fraction (example 2) to 0.134 mole fractions. The still pot bottoms (undistilled residue) are expected to contain propylene glycol, 1,2-butanediol and ethylene glycol recovered with trace amounts of water, and 2,3-Butanediol. FIG. 10 shows the lack of an azeotrope between ethanol and 2,3-butanediol (2,3-B-01).

Figure 5A:
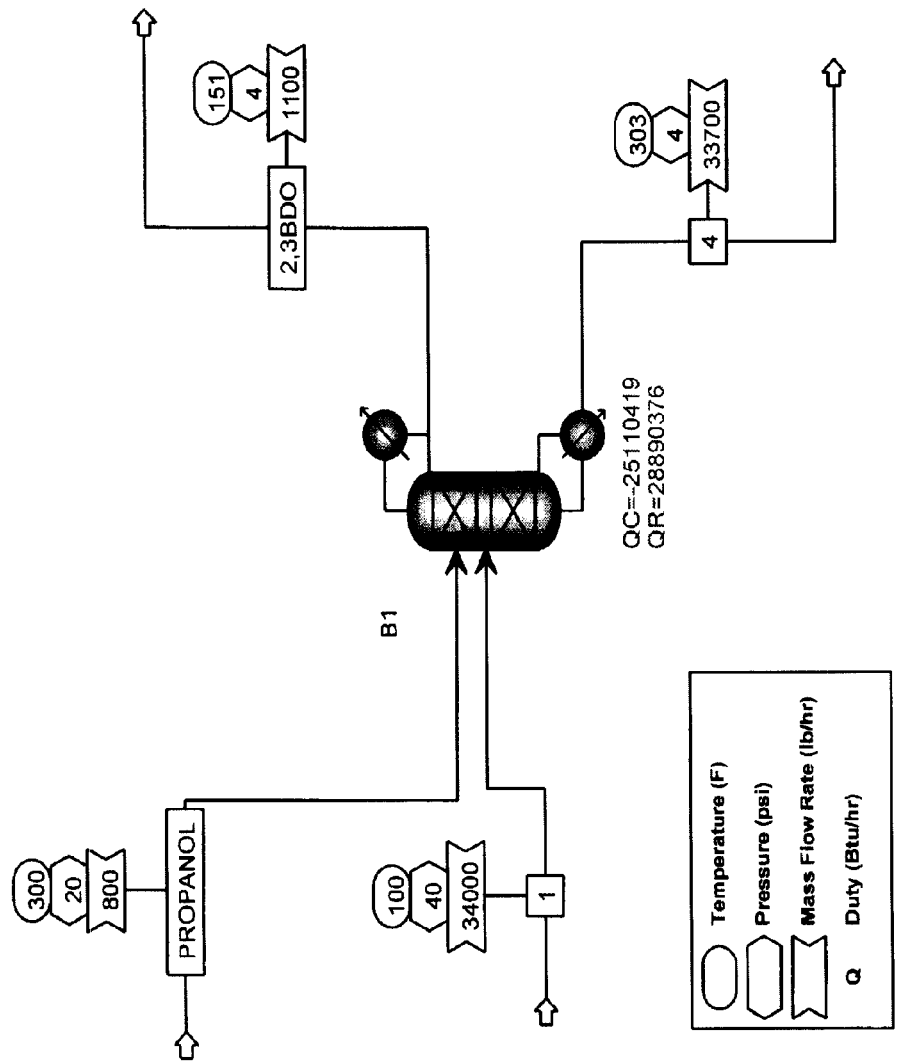
Figure 11:
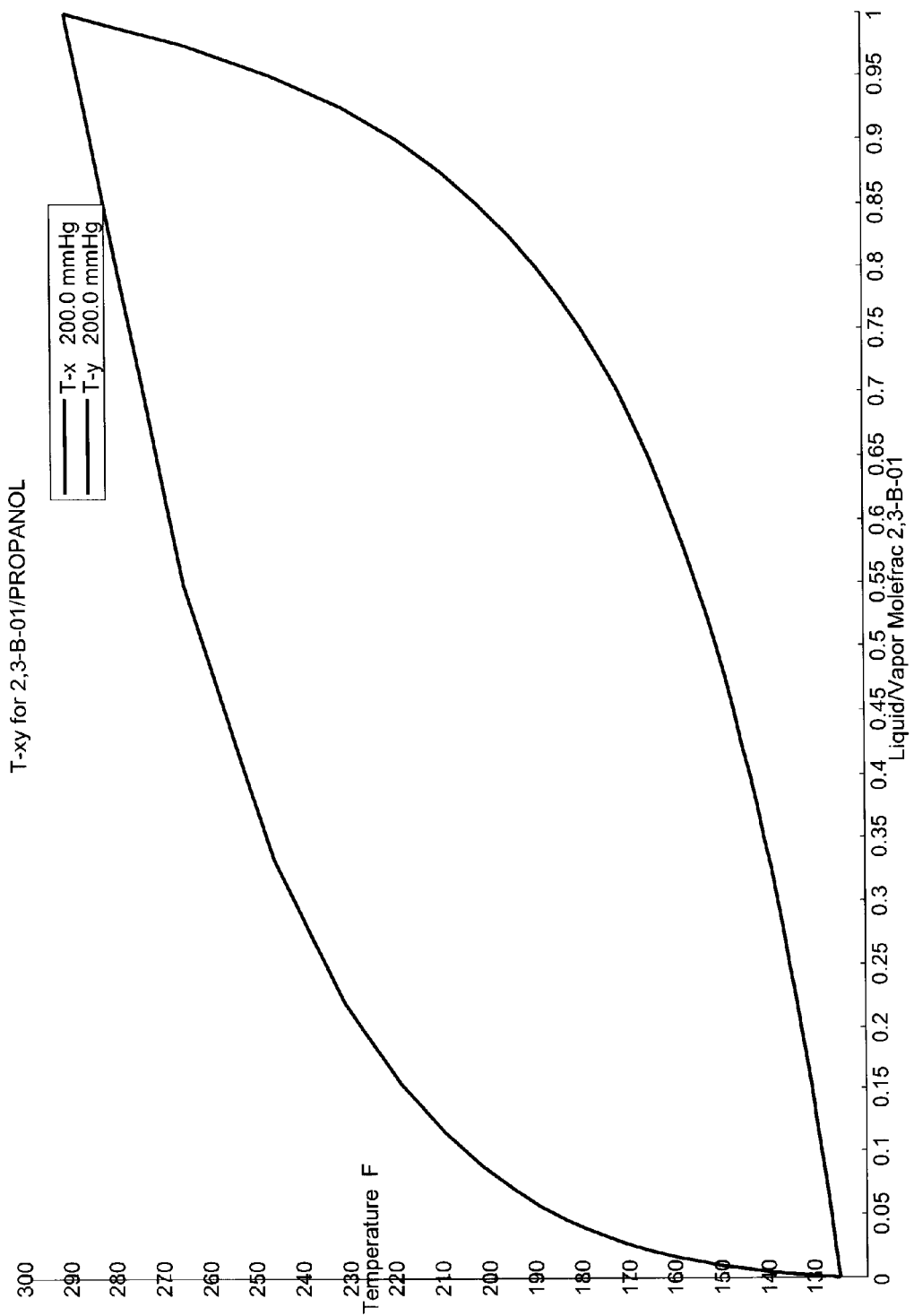
FIG. 11 depicts a graph indicating the lack of an azeotrope between n-propanol and 2,3-butanediol in one embodiment of the present invention.

Extractive distillation of a mixture of propylene glycol, ethylene glycol, 1,2-butanediol, 2,3-butanediol and trace amounts of water mixed with the polar solvent, n-propanol, to form a solution containing approximately 3.01% n-propanol to be distilled in a stainless steel structured packed column under reflux conditions was simulated substantially as described in example 2. As shown in FIG. 5B, the simulation predicted that the overheads would contain 0.146 mole fraction of propylene glycol and 0.096 mole fractions of 2,3-butanediol. Hence addition of the polar solvent, water, is expected to reduce the overhead loss of propylene glycol from 0.758 mole fraction (example 2) to 0.146 mole fractions. The simulation predicted that the still pot bottoms (undistilled residue) were propylene glycol, 1,2-butanediol and ethylene glycol recovered with trace amounts of water, and 2,3-butanediol. FIG. 11 shows the lack of an azeotrope between n-propanol and 2,3-butanediol (2,3-B-01).

Figure 6:
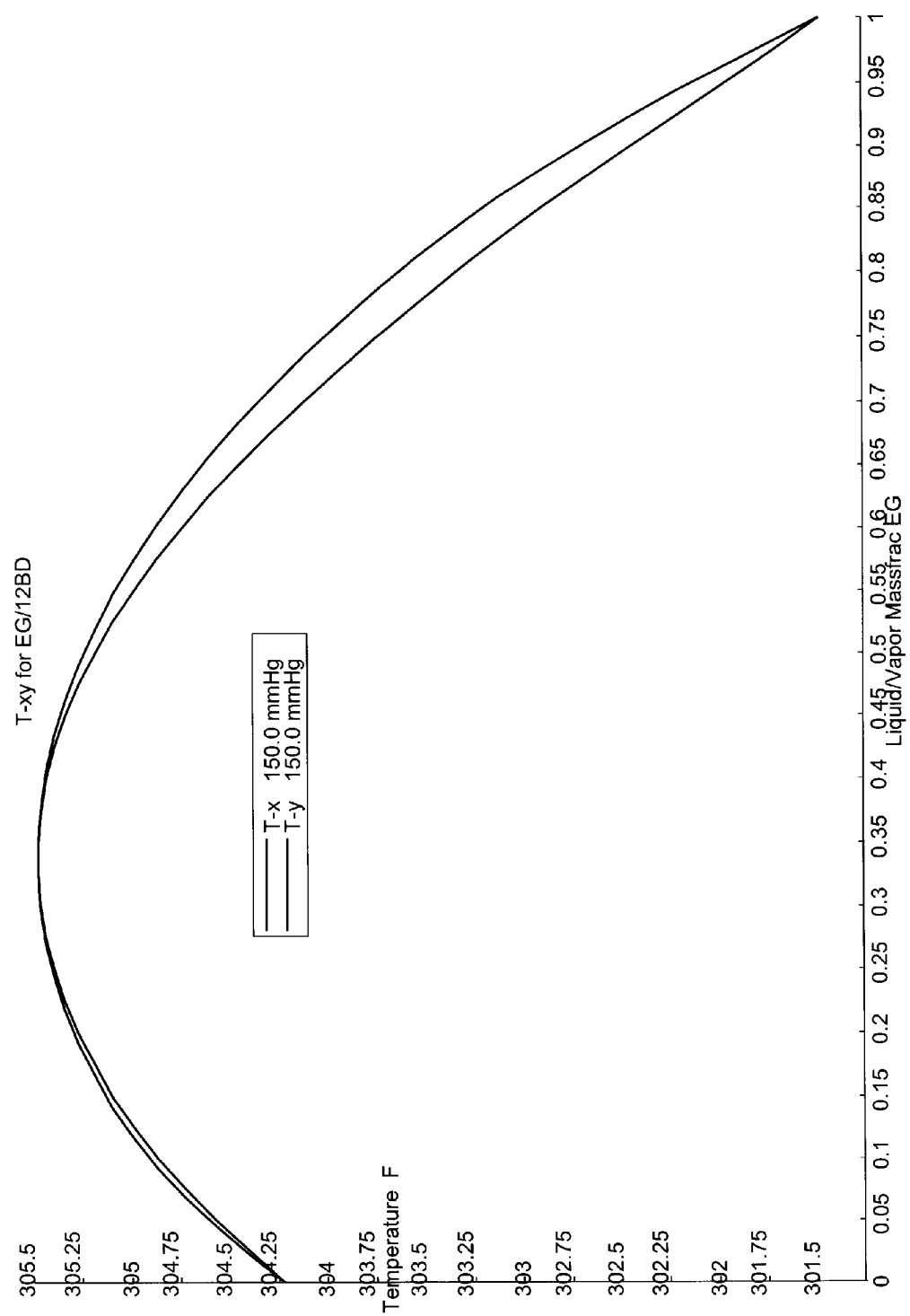
FIG. 6 depicts a graph indicating that 1,2-butanediol will form a high boiling azeotrope with ethylene glycol in one embodiment of the present invention.
Figure 7A:
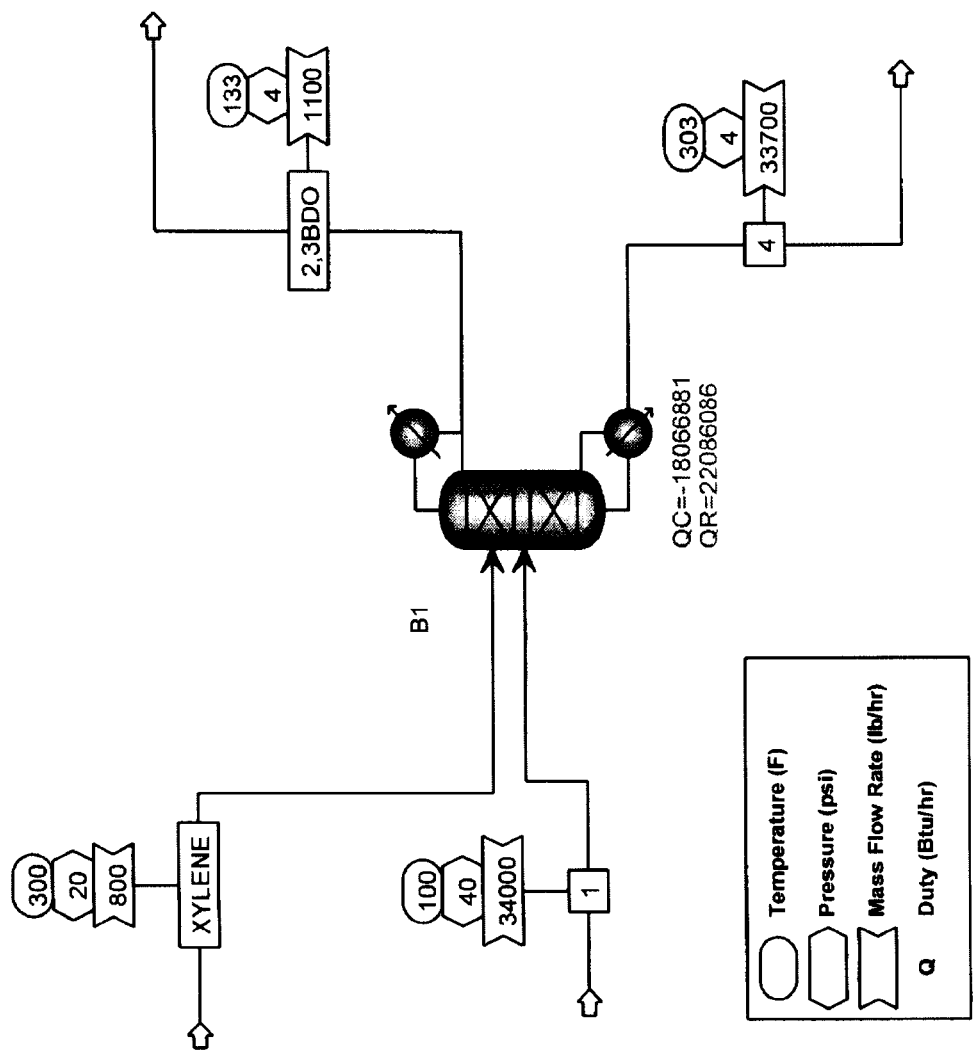

Extractive distillation of a mixture of propylene glycol, ethylene glycol, 1,2-butanediol, 2,3-butanediol and trace amounts of water mixed with the polar solvent, xylene, to form a solution containing approximately 1.79% xylene to be distilled in a stainless steel structured packed column under reflux conditions was simulated substantially as described in example 2. The model predicted that 1,2-butanediol will form a high boiling azeotrope with ethylene glycol (FIG. 6). As shown in FIG. 7B, the model predicted that the distillation overheads would contain 0.171 mole fraction of propylene glycol and 0.071 mole fraction of 2,3-butanediol. Hence addition of xylene and the resulting azeotrope was predicted to reduce the overhead loss of propylene glycol from 0.758 mole fraction (example 2) to 0.171 mole fractions. The model predicted that the still pot bottoms (undistilled residue) would include propylene glycol, 1,2-butanediol and ethylene glycol recovered with trace amounts of water, and 2,3-butanediol. The overheads also contained 0.727 moles of xylene that would need to be recovered from 2,3-butanediol in order to be recycled.

A mixture is obtained by hydrogenolysis of a carbohydrate. The mixture comprising propylene glycol, ethylene glycol, 1,2-butanediol, 2,3-butanediol and trace amounts of water is mixed with water to form a solution containing approximately 10% water. The mixture is extractively distilled in a stainless steel structured packed column under reflux conditions. It is expected that the overheads will contain about 0.092 mole fraction of propylene glycol and about 0.15 mole fraction of 2,3-butanediol, as shown in FIG. 2B. Hence addition of the polar solvent, water, is expected to reduce the overhead loss of propylene glycol from 0.758 mole fraction (example 2) to 0.092 mole fractions. The still pot bottoms (undistilled residue) would be expected to include propylene glycol, 1,2-butanediol and ethylene glycol that is recovered with trace amounts of water, and 2,3-butanediol. FIG. 8 shows the lack of an azeotrope between water and 2,3-butanediol.

A mixture of propylene glycol, ethylene glycol, 1,2-butanediol, 2,3-butanediol and trace amounts of water is mixed with methanol to form a solution containing approximately 5% methanol. The mixture is extractively distilled in a stainless steel structured packed column under reflux conditions. It is expected that the overheads will contain about 0.117 mole fraction of propylene glycol and about 0.124 mole fraction of 2,3-Butanediol, as shown in FIG. 3B. Hence addition of a polar solvent like water is expected to reduce the overhead loss of propylene glycol from 0.758 mole fraction (example 2) to 0.117 mole fractions. The still pot bottoms (undistilled residue) would be expected to include propylene glycol, 1,2-butanediol and ethylene glycol that is recovered with trace amounts of water, and 2,3-butanediol. FIG. 9 shows the lack of an azeotrope between methanol and 2,3-butanediol (2,3-B-01).

A mixture of propylene glycol, ethylene glycol, 1,2-butanediol, 2,3-butanediol and trace amounts of water is mixed with n-propanol to form a solution containing approximately 3.01% n-propanol. The solution is extractively distilled in a stainless steel structured packed column under reflux conditions. It is expected that the overheads will contain about 0.146 mole fraction of propylene glycol and about 0.096 mole fraction of 2,3-butanediol, as shown in FIG. 5B. Hence addition of a polar solvent like water is expected to reduce the overhead loss of propylene glycol from 0.758 mole fraction (example 2) to 0.146 mole fractions. The still pot bottoms (undistilled residue) would be expected to include propylene glycol, 1,2 Butanediol and Ethylene Glycol recovered with trace amounts of water, and 2,3-Butanediol. FIG. 11 shows the lack of an azeotrope between n-propanol and 2,3-butanediol (2,3-B-01).

A mixture of propylene glycol, ethylene glycol, 1,2-butanediol, 2,3-butanediol and trace amounts of water is mixed with xylene to form a solution containing approximately 1.79% xylene. The mixture is azeotropically distilled in a stainless steel structured packed column under reflux conditions. 1,2-Butanediol is expected to form a high boiling azeotrope with ethylene glycol (FIG. 6). It is expected that the distillation overheads will contain about 0.171 mole fraction of propylene glycol and about 0.071 mole fractions of 2,3-butanediol, as shown in FIG. 7B. Hence addition of xylene and the resulting azeotrope is expected to reduce the overhead loss of propylene glycol from 0.758 mole fraction (example 2) to 0.171 mole fractions. The still pot bottoms (undistilled residue) would be expected to include propylene glycol, 1,2-butanediol and ethylene glycol recovered with trace amounts of water, and 2,3-butanediol. The overheads would be expected to contain 0.727 moles of xylene that would need to be recovered from 2,3-butanediol in order to be recycled.

The present invention has been described with reference to certain exemplary embodiments, compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiment, but rather by the appended claims as originally filed.

What is claimed is:

1. A process for isolating or purifying bio-based propylene glycol, the process comprising:
   placing the bio-based propylene glycol, and a polar solvent in an apparatus;
   distilling the bio-based propylene glycol, and the polar solvent in the apparatus; and
   collecting the distilled bio-based propylene glycol, the distilled bio-based propylene glycol containing less than 0.2 weight percent of butanediols combined.

2. The process of claim 1, wherein the polar solvent is selected from the group consisting of methanol, ethanol, n-propanol, n-butanol, iso-butanol, amyl alcohol, water, acetone, lactic acid, acetic acid, butyric acid, gluconic acid, sulfuric acid, hydrochloric acid, and any combinations thereof.

3. The process of claim 1, further comprising subjecting the collected bio-based propylene glycol, to a further purification or isolation process.

4. The process of claim 1, wherein the polar solvent has; a Hansen P solubility parameter greater than 12, a Hansen H solubility parameter greater than 15, a ratio of the Hansen P solubility parameter to the Hansen H solubility parameter of less than 0.5, or any combination thereof.

5. The process of claim 1, further comprising producing the bio-based propylene glycol from bio-based glycerol.

* * * * *